United States Patent
Marin et al.

(10) Patent No.: US 7,335,711 B2
(45) Date of Patent: Feb. 26, 2008

(54) PREPARATION AND USE OF TETRASUBSTITUTED FLUORENYL CATALYSTS FOR POLYMERIZATION OF OLEFINS

(75) Inventors: Vladimir Marin, Houston, TX (US); Abbas Razavi, Mons (BE)

(73) Assignee: Fina Technology, Inc., Houston, TX (US)

( * ) Notice: Subject to any disclaimer, the term of this patent is extended or adjusted under 35 U.S.C. 154(b) by 150 days.

(21) Appl. No.: 11/205,934

(22) Filed: Aug. 17, 2005

(65) Prior Publication Data
US 2007/0043183 A1 Feb. 22, 2007

(51) Int. Cl.
*C08F 4/63012* (2006.01)
*C08F 4/64* (2006.01)

(52) U.S. Cl. ............... 526/160; 526/165; 526/348; 526/351; 526/943; 502/103; 502/152

(58) Field of Classification Search ............... 526/160, 526/165, 348, 351, 943; 502/103, 152
See application file for complete search history.

(56) References Cited

U.S. PATENT DOCUMENTS

| 4,767,735 | A | 8/1988 | Ewen et al. | |
|---|---|---|---|---|
| 5,155,080 | A | 10/1992 | Elder et al. | |
| 6,313,242 | B1 | 11/2001 | Reddy | |
| 6,469,188 | B1 | 10/2002 | Miller et al. | |
| 2006/0025299 | A1* | 2/2006 | Miller et al. | 502/103 |
| 2006/0161013 | A1* | 7/2006 | Tohi et al. | 556/11 |
| 2006/0270812 | A1 | 11/2006 | Tohi et al. | |

FOREIGN PATENT DOCUMENTS

WO WO 2004/029062 * 4/2004

* cited by examiner

*Primary Examiner*—Caixia Lu
(74) *Attorney, Agent, or Firm*—William D. Jackson; Diane L. Kilpatrick-Lee

(57) ABSTRACT

Catalyst compositions and processes for the polymerization of ethylenically unsaturated monomers to produce polymers, including copolymers or homopolymers. Such monomers include ethylene, $C_{3+}$ alpha olefins and substituted vinyl compounds, such as styrene and vinyl chloride. The polymerization catalyst characterized by the formula $B(FluL)MQ_n$ in which Flu is a fluorenyl group substituted at at least the 2,7- and 3,6-positions by hydrocarbyl groups, preferably relatively bulky hydrocarbyl groups. L is a substituted or unsubstituted cyclopentadienyl, indenyl or fluorenyl group or a heteroorgano group, XR, in which X is a heteroatom from Group 15 or 16 of the Periodic Table of Elements, such as nitrogen, R is an alkyl group, a cycloalkyl group or an aryl group and B is a structural bridge extending between the groups L and Flu, which imparts stereorigidity to the ligand structure, M is a Group 4 or Group 5 transition metal, such as titanium, zirconium or hafnium and Q is selected from the group consisting of chlorine, bromine, iodine, an alkyl group, an amino group, an aromatic group and mixtures thereof, with n being 1 or 2.

7 Claims, No Drawings

PREPARATION AND USE OF TETRASUBSTITUTED FLUORENYL CATALYSTS FOR POLYMERIZATION OF OLEFINS

FIELD OF THE INVENTION

This invention relates to olefin polymerization catalysts and their use in the polymerization of ethylenically unsaturated monomers.

BACKGROUND OF THE INVENTION

Olefin polymers such as polyethylene, polypropylene, which may be atactic or stereospecific, such as isotactic or syndiotactic, and ethylene-higher alpha olefin copolymers, such as ethylene-propylene copolymers can be produced under various polymerization conditions and employing various polymerization catalysts. Such polymerization catalysts include Ziegler-Natta catalysts and non-Ziegler-Natta catalysts, such as metallocenes and other transition metal catalysts which are typically employed in conjunction with one or more co-catalysts. The polymerization catalysts may be supported or unsupported.

The alpha olefin homopolymers or copolymers may be produced under various conditions in polymerization reactors which may be batch type reactors or continuous reactors. Continuous polymerization reactors typically take the form of loop-type reactors in which the monomer stream is continuously introduced and a polymer product is continuously withdrawn. For example, polymers such as polypropylene, polyethylene or ethylene-propylene copolymers involve the introduction of the monomer stream into the continuous loop-type reactor along with an appropriate catalyst system to produce the desired olefin homopolymer or copolymer. The resulting polymer is withdrawn from the loop-type reactor in the form of a "fluff" which is then processed to produce the polymer as a raw material in particulate form as pellets or granules. In the case of $C_{3+}$ alpha olefins, such a propylene or substituted ethylenically unsaturated monomers such as styrene or vinyl chloride, the resulting polymer product may be characterized in terms of stereoregularity, such as in the case of, for example, isotactic polypropylene or syndiotactic polypropylene.

The structure of isotactic polypropylene can be described as one having the methyl groups attached to the tertiary carbon atoms of successive monomeric units falling on the same side of a hypothetical plane through the main chain of the polymer, e.g., the methyl groups are all above or below the plane. Using the Fischer projection formula, the stereochemical sequence of isotactic polypropylene is described as follows:

(1)

In Formula 1, each vertical segment indicates a methyl group on the same side of the polymer backbone. Another way of describing the structure is through the use of NMR. Bovey's NMR nomenclature for an isotactic pentad as shown above is . . . mmmm . . . with each "m" representing a "meso" dyad, or successive pairs of methyl groups on the same said of the plane of the polymer chain. As is known in the art, any deviation or inversion in the structure of the chain lowers the degree of isotacticity and crystallinity of the polymer.

In contrast to the isotactic structure, syndiotactic propylene polymers are those in which the methyl groups attached to the tertiary carbon atoms of successive monomeric units in the chain lie on alternate sides of the plane of the polymer. Syndiotactic polypropylene using the Fisher projection formula can be indicated by racemic dyads with the syndiotactic pentad rrrr shown as follows:

(2)

Here, the vertical segments again indicate methyl groups in the case of syndiotactic polypropylene, or other terminal groups, e.g. chloride, in the case of syndiotactic polyvinyl chloride, or phenyl groups in the case of syndiotactic polystyrene.

Other unsaturated hydrocarbons which can be polymerized or copolymerized with relatively short chain alpha olefins, such as ethylene and propylene include dienes, such as 1,3-butadiene or 1,4-hexadiene or acetylenically unsaturated compounds, such as methylacetylene.

SUMMARY OF THE INVENTION

In accordance with the present invention, there are provided catalyst compositions and processes for the polymerization of ethylenically unsaturated monomers to produce polymers, including copolymers or homopolymers. Monomers, which are polymerized or copolymerized in accordance with the present invention, include ethylene, $C_{3+}$ alpha olefins and substituted vinyl compounds, such as styrene and vinyl chloride. A particularly preferred application of the invention is in the polymerization of propylene including the homopolymerization of propylene to produce polypropylene, preferably isotactic polypropylene and syndiotactic polypropylene having a high melting temperature, and the copolymerization of ethylene and a $C_{3+}$ alpha olefin to produce an ethylene alpha olefin copolymer, specifically an ethylene-propylene copolymer.

In carrying out the present invention, there is provided an olefin polymerization catalyst characterized by the formula:

$$B(FluL)MQ_n \qquad (3)$$

In formula (3), Flu is a fluorenyl group substituted at at least the 2,7- and 3,6-positions by hydrocarbyl groups, preferably relatively bulky hydrocarbyl groups. L is a substituted or unsubstituted cyclopentadienyl, indenyl or fluorenyl group or a heteroorgano group, XR, in which X is a heteroatom from Group 15 or 16 of the Periodic Table of Elements, and R is an alkyl group, a cycloalkyl group or an aryl group. Preferably X is nitrogen, phosphorus, oxygen or sulfur. More preferably, X will take the form of nitrogen. R is an alkyl group or cycloalkyl group containing from 1 to 20 carbon atoms, or a mononuclear aromatic group which may be substituted or unsubstituted. Further, with respect to formula (3), B is a structural bridge extending between the groups L and Flu, which imparts stereorigidity to the ligand structure. Preferably, the bridge B is characterized by the formula $ER^1R^2$, in which E is a carbon, silicon or germanium atom, and $R^1$ and $R^2$ are each independently a hydrogen, a $C_1$-$C_{10}$ alkyl group, an aromatic group or a cycloalkyl group. Further, with respect to formula (3), M is a Group 4 or Group 5 transition metal, preferably titanium, zirconium or hafnium. Q is selected from the group consisting of chlorine, bromine, iodine, an alkyl group, an amino group, an aromatic group and mixtures thereof, n is 1 or 2 and will have a value of 2 where the transition metal is zirconium, hafnium or titanium.

In one embodiment of the invention, the fluorenyl group Flu is substituted with an aryl group at each of the 2- and 7-positions and with a lower molecular weight substituent at each of the 3- and 6-positions. More specifically, the fluorenyl group is substituted at the 2- and 7-positions with a phenyl or substituted phenyl group and at each of the 3- and 6-positions with a bulky hydrocarbyl group containing at least 4 carbon atoms. Preferably, the bulky hydrocarbyl group at the 3- and 6-positions is a tertiary butyl group.

In the embodiment of the invention in which the metallocene component is substituted at the 2- and 7-positions with an aryl group as described above and at the 3- and 6-positions with a tertiary butyl group, the metallocene component is characterized by the formula:

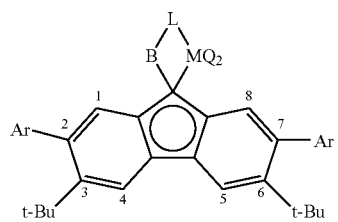

(4)

wherein Ar is a phenyl group or substituted phenyl group.

In a specific embodiment of the invention in which the ligand component L is a heteroorgano group, the metallocene component is characterized by the formula:

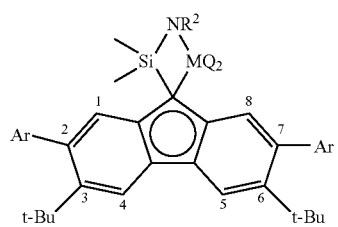

(5)

wherein Ar is a phenyl group or a substituted phenyl group, and R is an alkyl group having from 1 to 20 carbon atoms or an aryl group having from 6 to 20 carbon atoms.

In a further embodiment of the invention in which the metallocene component incorporates a cyclopentadienyl group, the metallocene is characterized by the formula:

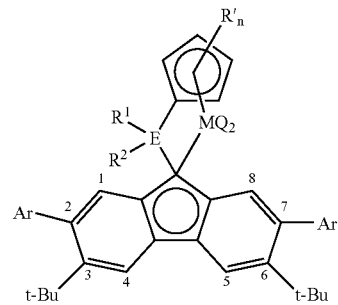

(6)

In formula (6), Ar is a phenyl group or substituted phenyl group, R' is a $C_1$-$C_4$ alkyl group or an aryl group, n is the number of substituents, from 0 to 4, E is a —C— group or an —Si— group, $R^1$ and $R^2$ are each independently a hydrogen, a $C_1$-$C_{10}$ alkyl group, or a cycloalkyl group, or an aryl group, M is titanium, zirconium or hafnium, and Q is chlorine, a methyl group or a phenyl group. Preferably, in formula (6), the cyclopentadienyl group is unsubstituted, disubstituted or tetra-substituted to provide a metallocene component which exhibits bilateral symmetry. In another embodiment of the invention, however, the cyclopentadienyl group is monosubstituted or trisubstituted to provide a metallocene component which exhibits non-bilateral symmetry.

In yet a further embodiment of the invention, the metallocene component incorporates a cyclopentadienyl group which is substituted with a methyl group and a tertiary butyl group to provide a metallocene component characterized by the formula:

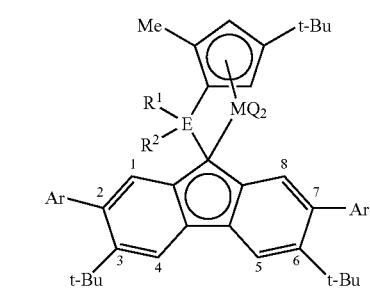

(7)

In formula (7), Ar is a phenyl group or substituted phenyl group, E is a —C— group or an —Si— group, $R^1$ and $R^2$ are each independently a hydrogen, a $C_1$-$C_{10}$ alkyl group, or a cycloalkyl group, or an aryl group, M is titanium, zirconium or hafnium, and Q is chlorine, a methyl group or a phenyl group.

In yet a further embodiment of the invention, the metallocene component incorporates an unsubstituted cyclopentadienyl group and is characterized by the formula:

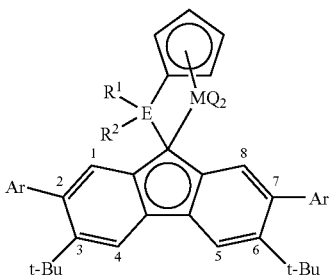

(8)

In formula (8), Ar is a phenyl group or substituted phenyl group, $R^1$ and $R^2$ are each independently a hydrogen, a $C_1$-$C_{10}$ alkyl group, or a cycloalkyl group, or an aryl group, E is a —C— group or an —Si— group, M is titanium, zirconium or hafnium, and Q is chlorine, a methyl group or a phenyl group.

Another embodiment of the invention involves a metallocene catalyst component which incorporates an indenyl group and is characterized by the formula:

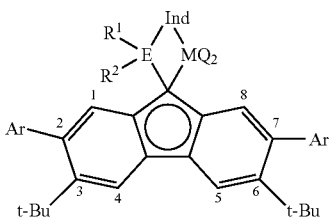

(9)

In formula (9), Ar is a phenyl group or substituted phenyl group, Ind is an indenyl or substituted indenyl group, E is a —C— group or an —Si— group, each of $R^1$ and $R^2$ is independently a hydrogen, a $C_1$-$C_{10}$ alkyl group, a cycloalkyl group or an aryl group, M is titanium, zirconium or hafnium, and Q is chlorine, a methyl group or a phenyl group. In this aspect of the invention, the indenyl group may be a tetrahydroindenyl group which is substituted or unsubstituted.

In another aspect of the invention in which the secondary ligand component L is a fluorenyl group, the metallocene component is characterized by the formula:

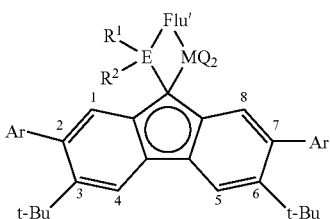

(10)

In formula (10), Flu' is a fluorenyl or a substituted fluorenyl group, E is a —C— group or an —Si— group, each of $R^1$ and $R^2$ is a $C_1$-$C_4$ alkyl group, M is titanium, zirconium or hafnium, and Q is chlorine, a methyl group or a phenyl group. Preferably, the fluorenyl group Flu' in formula (10) is an unsubstituted fluorenyl group or a substituted fluorenyl group wherein the metallocene component exhibits bilateral symmetry.

In yet a further aspect of the invention, there is provided a process for the polymerization of one or more ethylenically unsaturated monomers to produce a corresponding homopolymer or copolymer. In carrying out the polymerization process, there is provided a metallocene catalyst component as characterized by the above formula (3). In addition to the metallocene catalyst component, there is provided an activating cocatalyst component. The catalyst component and the cocatalyst component are contacted in a polymerization reaction zone with an ethylenically unsaturated monomer under polymerization conditions to produce a polymer product which is then recovered from the reaction zone. Preferably, the activating co-catalyst comprises methylalumoxane (MAO) or tri-isobutylalumoxane (TIBAO) or mixtures thereof. Alternatively, the activating co-catalyst can take the form of a noncoordinating anionic type, such as triphenylcarbenium tetrakis(pentafluorophenyl)aluminate or triphenylcarbenium tetrakis(pentafluorophenyl)boronate. Preferably, the ethylenically unsaturated monomer is a $C_{3+}$ alpha olefin. More specifically, the alpha olefin is propylene and the polymerization reaction is carried out to produce syndiotactic or isotactic polypropylene.

In a preferred embodiment of the invention, the metallocene component incorporates a cyclopentadienyl group and is characterized by the formula:

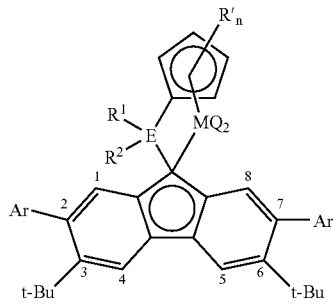

(11)

In formula (11), Ar is a phenyl group or substituted phenyl group, $R^1$ and $R^2$ are each independently a hydrogen, a $C_1$-$C_{10}$ alkyl group, or a cycloalkyl group, or an aryl group, R' is a $C_1$-$C_4$ alkyl group or an aryl group, n is a number from 0 to 4, E is a —C— group or an —Si— group, each of $R_1$ and $R_2$ is a $C_1$-$C_4$ alkyl group, M is titanium, zirconium or hafnium, and Q is chlorine, a methyl group, a phenyl group, or a substituted phenyl or benzyl group. In one aspect of this embodiment of the invention, the metallocene component exhibits bilateral symmetry and the polymer product is syndiotactic polypropylene. In another aspect, the metallocene does not exhibit bilateral symmetry and the polymer product is isotactic polypropylene. In a specific embodiment of the process, the metallocene component incorporates an unsubstituted cyclopentadienyl group and is characterized by the formula:

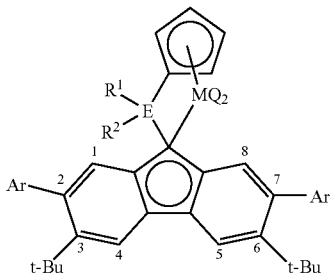

(12)

to produce a syndiotactic polypropylene having a melting temperature higher than 150° C. and a crystallization temperature of more than 95° C. Preferably, the syndiotactic polypropylene has a melting temperature greater than 170° C.

DETAILED DESCRIPTION OF INVENTION

The present invention involves bridged transition metal catalysts having metallocene ligand structures incorporating tetra-substituted fluorenyl groups and their use in the polymerization of olefins. Specific olefins which may be polymerized, either through homopolymerization or copolymerization include ethylene, propylene, butylene, as well as monoaromatic or substituted vinyl compounds as described previously. The bridged catalyst components of the present invention incorporate transition metals from Groups 4 or 5 of the Periodic Table of Elements (new notation) and more particularly, transition metals from Group 4 of the Periodic Table of Elements. Preferred transition metals for use in the catalyst components of the present invention are titanium, zirconium and hafnium, with zirconium being particularly preferred.

The catalyst components of the present invention incorporate a primary fluorenyl group that is tetra-substituted fluorenyl group which is bridged to a secondary ligand structure which is a substituted or unsubstituted cyclopentadienyl, indenyl or fluorenyl group or a heteroorgano group. The tetra-substituted fluorenyl groups are symmetrical with respect to a plane of symmetry through the bridge and the transition metal. Preferably, the substituents at the 2,7 positions are bulkier than the substituents at the 3,6 positions. However, a reverse relationship of substitution may be employed in some instances. In this case, the primary fluorenyl group may be substituted at the 2- and 7-positions with a $C_1$-$C_3$ alkyl group and at the 3- and 6-positions with a bulky hydrocarbyl group containing at least 4 carbon atoms. More specifically, the catalyst components of the present invention comprise metallocene ligand structures which incorporate tetra-substituted fluorenyl groups substituted at at least the 2,7 and 3,6 positions which are bridged to substituted or unsubstituted cyclopentadienyl, indenyl, fluorenyl or heteroorgano groups and which are characterized in terms of symmetry (or asymmetry) with reference to a plane of symmetry extending through the bridge and the transition metal.

The following diagrams indicate metallocene ligand structures (and the numbering schemes for such structures) which may be employed in carrying out the present invention. Diagram (13) indicates a cyclopentadienyl-fluorenyl ligand structure, diagram (14) an indenyl-fluorenyl ligand structure, diagram (15) a heteroatom (XR)-fluorenyl ligand structure, and diagram (16) a fluorenyl-fluorenyl ligand structure.

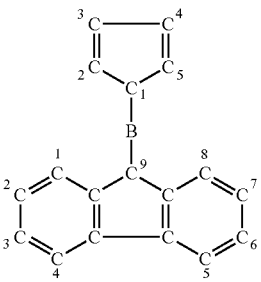

(13)

(14)

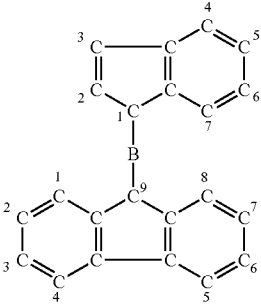

(15)

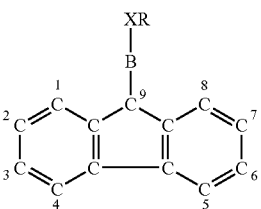

(16)

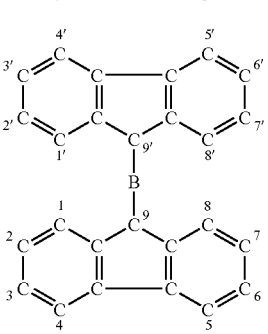

The numbering schemes used to indicate the position of substituents on the various ligand structures are indicated on diagrams (13)-(16). With respect to structure (14), while not shown, the indenyl moiety may take the form of 4,5,6,7-tetrahydro indenyl as well as the more common unhydrogenated indenyl group. For each of diagrams (13)-(16), the metallocene ligand structures may be characterized in terms of a plane of symmetry extending perpendicular to the plane of the paper through the bridge group B and the transition metal (not shown) in diagrams (13)-(16) which would project upwardly from the plane of the paper.

As described with respect to various examples given below and with respect, for example, to diagram (13), the cyclopentadienyl group may be monosubstituted and the fluorenyl group may be symmetrically substituted at the 2,7 and 3,6 positions. If there are no other substituents or if the fluorenyl group is otherwise symmetrically substituted, the 3-position is equivalent to the 4-position on the cyclopentadienyl group and this relationship may be expressed by the positional expression 3(4).

The catalysts of the present invention can be advantageously used in propylene polymerization to produce syndiotactic or isotactic polypropylenes with high yields, having high molecular weights, high tacticities and high melt temperatures. Desired features of the catalysts of the present invention are due to a unique combination of structural parameters of the catalysts and substitutions of the cyclopentadienyl and fluorenyl rings. In addition, the catalysts of the present invention can be used in copolymerization of propylene with olefins, e.g. ethylene to yield random or impact copolymers.

Ligand structures suitable for use in carrying out the present invention which can be employed to produce isotactic polypropylene include, with reference to diagram (13), 3-tertiary butyl, 5-methyl cyclopentadienyl, 2,7-ditertiary butyl, 4-phenyl fluorene, the same ligand structure except with substitution on the fluorenyl structure at the 5-position and the same ligand structure with substitution at the 4- or 5-positions by a 4-tertiary butyl phenyl group. In other words, the phenyl group is substituted by a tertiary butyl group at the directly distal position with respect to the substitution of the phenyl group on the fluorenyl group.

Other suitable ligand structures which can be employed to produce isotactic polypropylene include ligand structures such as described above, except the cyclopentadienyl group is mono-substituted at the 3-position with a tertiary butyl group. The fluorenyl group is substituted as before at the 2- and 7-positions with the tertiary butyl groups and at the 4-position with a phenyl group or a 4-tertiary butyl phenyl group.

Similarly substituted ligand structures may be employed in accordance with the present invention incorporating a bis-indenyl fluorenyl ligand structure exemplified by diagram (14). Typically, because of the unbalanced characteristic of the indenyl structure, further substitution of the indenyl (or the 4,5,6,7-tetrahyrdo indenyl) group will not be employed. The fluorenyl ligand component may be substituted as described previously, thus, it may be substituted at the 4-position or di-substituted at the 4- and 5-positions with bulky groups such as tertiary butyl and phenyl groups. Also, the fluorenyl ligand structure may be substituted at one of the 4- and 5-positions and disubstituted at the 2- and 7-positions with substituent groups which are less bulky than the substituents on the 4- or 5-positions.

The heteroatom ligand structure depicted in diagram (15) may be substituted on the fluorenyl group similarly as described above with respect to diagrams (13) and (14). Thus, for example, the fluorenyl group may be substituted at the 2- and 7-positions with tertiary butyl groups and substituted at the 4-position with a substituted or unsubstituted phenyl group. Alternatively, the fluorenyl group may be unsubstituted at the 2- and 7-positions and substituted at the 4-position with an isopropyl group, a tert-butyl group, a phenyl group or a substituted phenyl group.

In employing the catalyst components of the present invention in polymerization procedures, they are used in conjunction with an activating co-catalyst. Suitable activating co-catalysts may take the form of co-catalysts such are commonly employed in metallocene-catalyzed polymerization reactions. Thus, the activating co-catalyst may take the form of an aluminum co-catalyst. Alumoxane co-catalysts are also referred to as aluminoxane or polyhydrocarbyl aluminum oxides. Such compounds include oligomeric or polymeric compounds having repeating units of the formula:

(17)

where R is an alkyl group generally having 1 to 5 carbon atoms. Alumoxanes are well known in the art and are generally prepared by reacting an organo-aluminum compound with water, although other synthetic routes are known to those skilled in the art. Alumoxanes may be either linear polymers or they may be cyclic, as disclosed for example in U.S. Pat. No. 4,404,344. Thus, alumoxane is an oligomeric or polymeric aluminum oxy compound containing chains of alternating aluminum and oxygen atoms whereby the aluminum carries a substituent, preferably an alkyl group. The structure of linear and cyclic alumoxanes is generally believed to be represented by the general formula —(Al(R)—O—)-m for a cyclic alumoxane, and $R_2Al$—O—(Al(R)—O)$_m$—$AlR^2$ for a linear compound wherein R independently each occurrence is a $C_1$-$C_{10}$ hydrocarbyl, preferably alkyl or halide and m is an integer ranging from 1 to about 50, preferably at least about 4. Alumoxanes also exist in the configuration of cage or cluster compounds. Alumoxanes are typically the reaction products of water and an aluminum alkyl, which in addition to an alkyl group may contain halide or alkoxide groups. Reacting several different aluminum alkyl compounds, such as, for example, trimethylaluminum and tri-isobutylaluminum, with water yields so-called modified or mixed alumoxanes. Preferred alumoxanes are methylalumoxane and methylalumoxane modified with minor amounts of other higher alkyl groups such as isobutyl. Alumoxanes generally contain minor to substantial amounts of the starting aluminum alkyl compounds. The preferred co-catalyst, prepared either from trimethylaluminum or tri-isobutylaluminum, is sometimes referred to as poly (methylaluminum oxide) and poly (isobutylaluminum oxide), respectively.

The alkyl alumoxane co-catalyst and transition metal catalyst component are employed in any suitable amounts to provide an olefin polymerization catalyst. Suitable aluminum transition metal mole ratios are within the range of 10:1 to 20,000:1 and preferably within the range of 100:1 to 5,000:1. Normally, the transition metal catalyst component and the alumoxane, or other activating co-catalyst as described below, are mixed prior to introduction in the polymerization reactor in a mode of operation such as described in U.S. Pat. No. 4,767,735 to Ewen et al. The polymerization process may be carried out in either a batch-type, continuous or semi-continuous procedure, but preferably polymerization of the olefin monomer (or monomers) will be carried out in a loop type reactor of the type disclosed in the aforementioned U.S. Pat. No. 4,767,735. Typical loop type reactors include single loop reactors or so-called double loop reactors in which the polymerization procedure is carried in two sequentially connected loop reactors. As described in the Ewen et al. patent, when the catalyst components are formulated together, they may be supplied to a linear tubular pre-polymerization reactor where they are contacted for a relatively short time with the pre-polymerization monomer (or monomers) prior to being introduced into the main loop type reactors. Suitable contact times for mixtures of the various catalyst components prior to introduction into the main reactor may be within the range of a few seconds to 2 days. For a further description of suitable continuous polymerization processes which may be employed in carrying out the present invention, reference is made to the aforementioned U.S. Pat. No. 4,767,735, the entire disclosure of which is incorporated herein by reference.

Other suitable activating co-catalysts which can be used in carrying out the invention include those catalysts which function to form a catalyst cation with an anion comprising one or more boron atoms. By way of example, the activating co-catalyst may take the form of triphenylcarbenium tetrakis (pentafluorophenyl) boronate as disclosed in U.S. Pat. No. 5,155,080 to Elder et al. As described there, the activating co-catalyst produces an anion which functions as a stabilizing anion in a transition metal catalyst system. Suitable noncoordinating anions include $[W(PhF_5)]^-$, $[Mo(PhF_5)]^-$ (wherein $PhF_5$ is pentafluorophenyl), $[ClO_4]^-$, $[S_2O_6]^-$, $[PF_6]^-$, $[SbR_6]^-$, $[AlR_4]^-$ wherein each R is independently Cl, a $C_1$-$C_5$ alkyl group preferably a methyl group, an aryl group, e.g. a phenyl or substituted phenyl group, or a fluorinated aryl group). Following the procedure described in the Elder et al. patent, triphenylcarbenium tetrakis(pentafluorophenyl) boronate may be reacted with pyridinyl-linked bis-amino ligand of the present invention in a solvent, such as toluene, to produce a coordinating cationic-anionic complex. For a further description of such activating co-catalyst, reference is made to the aforementioned U.S. Pat. No. 5,155,080, the entire disclosure of which is incorporated herein by reference.

In addition to the use of an activating co-catalyst, the polymerization reaction may be carried out in the presence of a scavenging agent or polymerization co-catalyst which is added to the polymerization reactor along with the catalyst component and activating co-catalyst. These scavengers can be generally characterized as organometallic compounds of metals of Groups 1A, 2A, and 3B of the Periodic Table of Elements. As a practical matter, organoaluminum compounds are normally used as co-catalysts in polymerization reactions. Specific examples include triethylaluminum, tri-isobutylaluminum, diethylaluminum chloride, diethylaluminum hydride and the like. Co-catalysts normally employed in the invention include methylalumoxane (MAO), triethylaluminum (TEAL) and tri-isobutylaluminum (TIBAL).

The bridged fluorenyl ligand structures and the corresponding transition metal catalyst components can be prepared by any suitable techniques. Typically, for methylene bridged cyclopentadienyl fluorenyl ligand structures, the fluorenyl group is treated with methyl lithium to result in a fluorenyl group substituted with lithium in the 9-position and this is then reacted with a 6,6-substituted fulvene. For example, 6,6-dimethyl fulvene may be employed to produce the isopropylidene cyclopentadienyl substituted fluorenyl ligand structure. For a ligand structure in which the bridge group incorporates a germanium or silicon atom, the lithiumated fluorenyl group is reacted, for example, with diphenylsilyl dichloride to produce the diphenylsilyl chloride substituent at the 9-position on the fluorenyl group. This component is then reacted with the lithiumated cyclopentadienyl or substituted cyclopentadienyl to produce the bridge. The ligand structure is then treated with methyl lithium, followed by reaction with the appropriate transition metal, chlorine, e.g. zirconium tetrachloride, to produce the corresponding metallocene dichloride.

The catalyst components employed in the present invention can be prepared by techniques, which include procedures well-known in the art with appropriate modification of the fluorenyl ligand component to incorporate a 2,7,3,6-tetra-substituted fluorene. For example, as described below, 6,6-dimethyl fulvene can be employed in conjunction with 2,7,3,6 symmetrically substituted fluorene in order to produce the corresponding methylene-bridged cyclopentadienyl 2,7,3,6-tetra-substituted fluorene. The fluorenyl-fluorenyl ligand structures employed in the present invention can be synthesized using a procedure such as disclosed in U.S. Pat. No. 6,313,242 to Reddy to form bis-fluorenyl ligands, again with the qualification that a symmetrical ligand structure rather than the staggered ligand structure of the type disclosed in Reddy will be produced. Similarly, a bridged fluorenyl heteroatom ligand structure of the type characterized by formula 10 above can be produced by preparation of a substituted fluorene with dimethyldichlorosilane, followed by reaction with a tertiary butyllithiumamide to produce the bridged fluorenyl amine structure. Again, the above procedure would be followed, but with the modification to employ, for example, 2,7-diphenyl,3,6-ditertiary butyl fluorene rather than the 3,6-ditertiary butyl fluorene disclosed in the Reddy patent. The various procedures which can be used in the synthesis of the metallocene components of the present invention are illustrated by the synthesis procedures described below.

Specific metallocenes embodying the present invention are illustrated by the following structural formulas in which the isopropylidene bridge group is illustrated by ✕and a tertiary butyl group is indicated by ⊀.

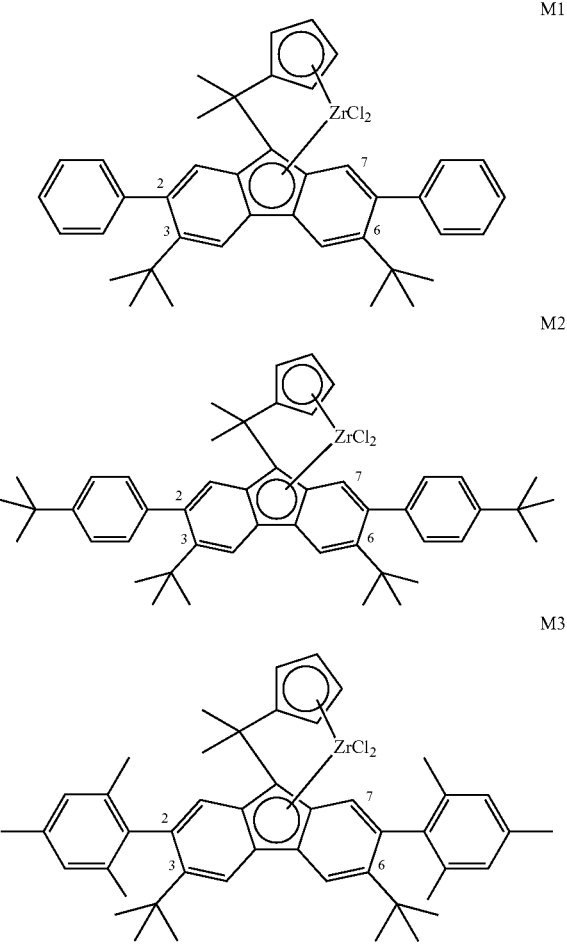

-continued
M4
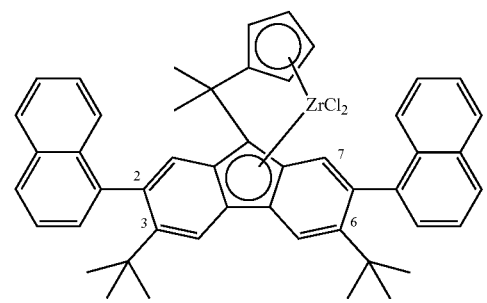
M5
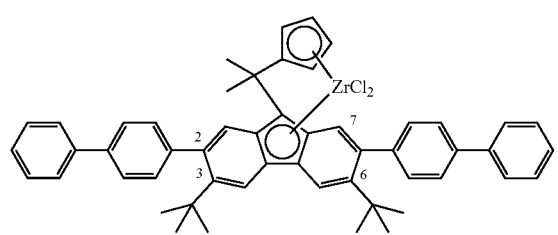
M6
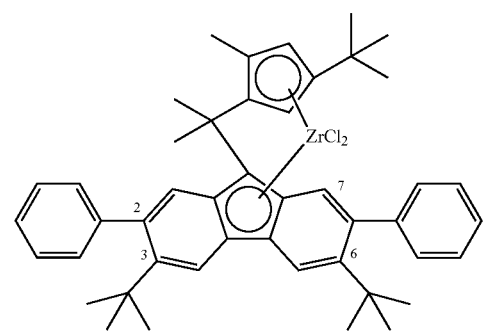
M7
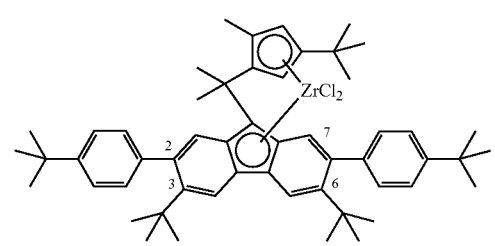
M8
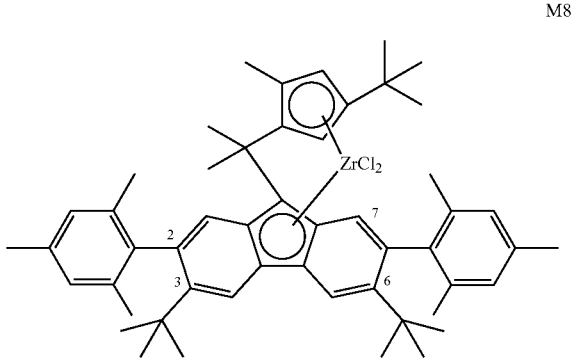
-continued
M9
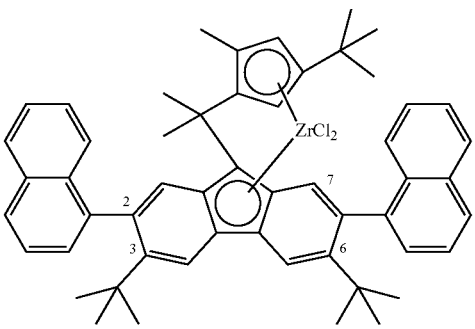
M10
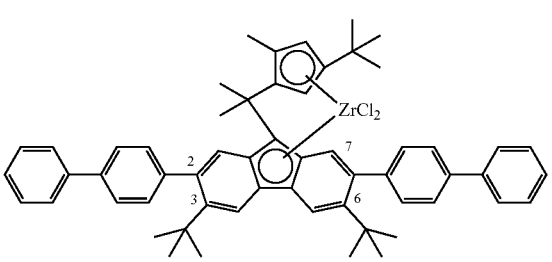
M11
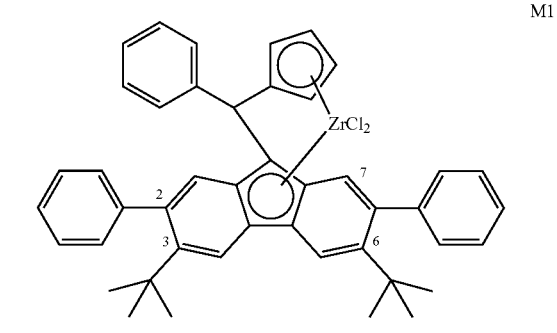
M12
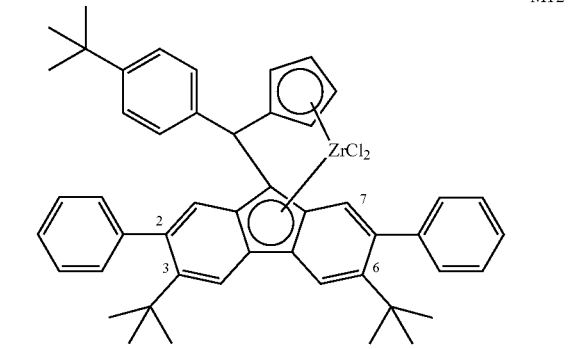
M13
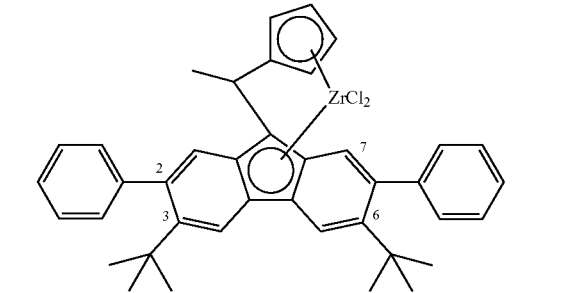

-continued

M14
M15
M16
M17
M18

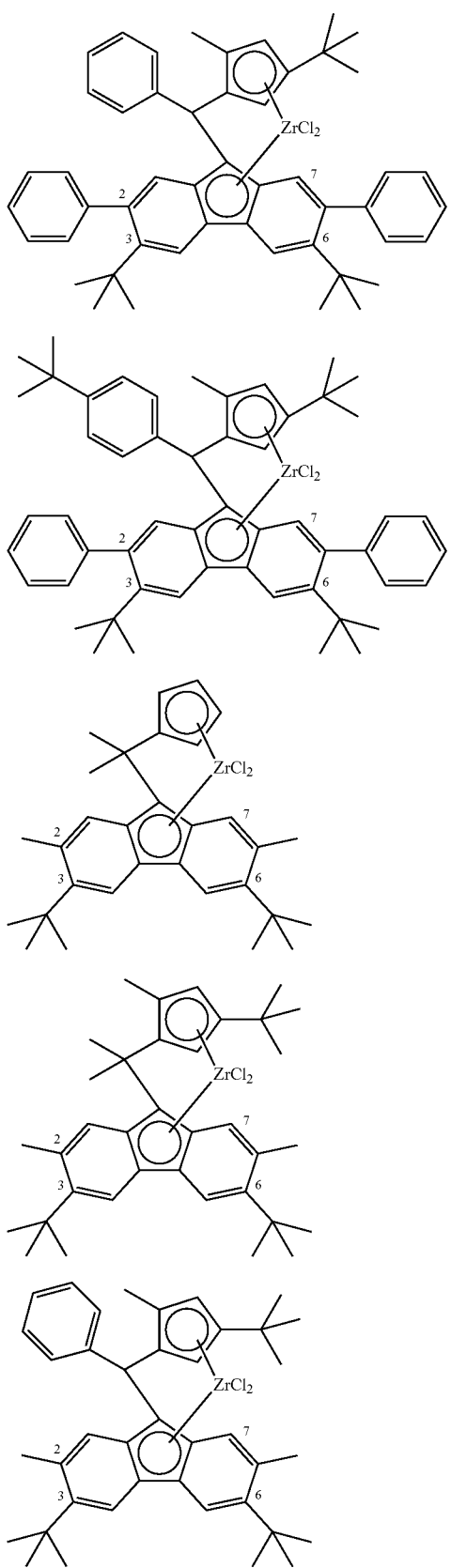

1. Synthesis of Catalysts 2,7-Dibromo-3,6-di-t-butyl-fluorene was synthesized by the reaction of 3,6-di-t-butyl-fluorene with N-bromo succinimide in propylene carbonate solution in 82% yield in accordance with the following reaction and used as a starting material for the synthesis of 2,7-di-aryl-3,6-di-tert-butyl-fluorenes for catalysts M1-M15:

(18)

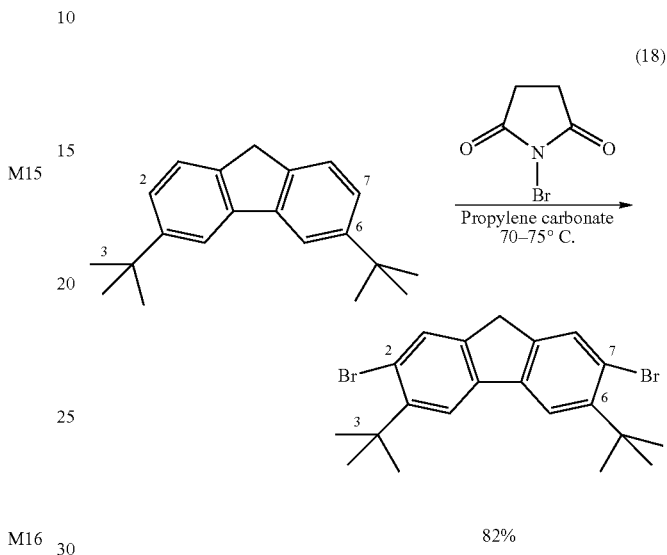

82%

The coupling reaction of 2,7-dibromo-3,6-di-t-butyl-fluorene with phenyl boronic acid provided 2,7-phenyl-3,6-di-t-butyl-fluorene in 90% yield in accordance with the following reaction:

EXAMPLE 1

Synthesis of 2,7-Dibromo-3,6-di-t-butyl-fluorene

To a solution of 3,6-di-t-butylfluorene (2.10 g, 7.55 mmol) in propylene carbonate (60 ml) was added 2.70 g of N-bromosuccinimide. The reaction mixture was stirred for 6 hours at 70-75° C. The mixture was poured into water and the precipitated solid was filtered, washed with water and dried to produce a yield of 2.71 g (82%). $^1$H NMR (CDCl$_3$): δ 7.80 and 7.72 (each s, 2H, 1,8- and 4,5-H (Flu), 3.74 (s, 2H, H9), 1.59 (s, 18H, t-Bu).

The coupling reaction of 2,7-dibromo-3,6-di-t-butyl-fluorene with aryl boronic acid produced 2,7-aryl-3,6-di-t-butyl-fluorene in an 85-95% yield in accordance with the following reaction:

(19)

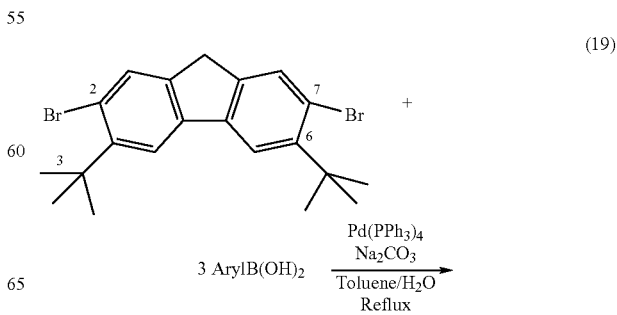

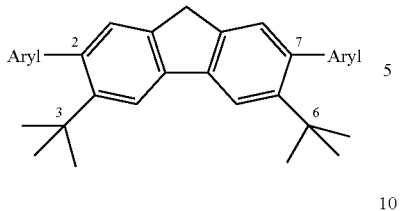

EXAMPLE 2

Synthesis of 2,7-Diphenyl-3,6-di-t-butyl-fluorene

To a mixture of 2,7-dibromo-3,6-di-t-butylfluorene (0.96 g, 2.20 mmol) and Pd(PPh$_3$)$_4$ (260 mg, 0.22 mmol) in toluene (50 ml) was added a solution of phenylboronic acid (0.81 g, 6.63 mmol) in EtOH (10 ml) and a solution of Na$_2$CO$_3$ (1.5 g) in water (10 ml). The reaction mixture was stirred for 6 hours under reflux. The reaction mixture was quenched with water, extracted with ether, dried over MgSO$_4$, and evaporated under vacuum to afford the residue which was purified by column chromatography (silica gel, hexane/CH$_2$Cl$_2$=5/1) to produce 2,7-diphenyl-3,6-di-t-butyl-fluorene (0.85 g, ~90%). $^1$H NMR (CDCl$_3$): δ 7.96 and 7.15 (each s, 2H, 1,8- and 4,5-H (Flu), 7.33 (m, 10H, Ph), 3.77 (s, 2H, H9), 1.27 (s, 18H, t-Bu).

EXAMPLE 3

Synthesis of 2,7-Di(4-tert-butyl-phenyl)-3,6-di-t-butyl-fluorene

The same procedure as in Example 2 was used except 4-tert-butyl-phenyl-boronic acid was used in place of phenylboronic acid. The yield was 92%.

The following Examples 4 and 5 illustrate the preparation of 2,7-dimethyl-3,6-di-tert-butyl-fluorene.

EXAMPLE 4

Synthesis of 2,7-dichloromethane-3,6-di-tert-butyl-fluorene

To a solution of 3,6-di-t-butylfluorene (2.00 g, 7.19 mmol) and chloromethyl methyl ether (2.5 ml) in CS$_2$ (15 ml) was added at 0° C. a solution of TiCl$_4$ (0.4 ml) in CS$_2$ (5 ml). The reaction mixture was stirred for 3 hours at room temperature. The mixture was poured into ice water and extracted with ether. The ether extract was dried over sodium sulfate and evaporated under vacuum to leave a residue, which was purified by column chromatography (hexane/CH$_2$Cl$_2$=10/1) and crystallization from hot heptanes. The product provided 2-chloromethyl-3,6-di-t-butylfluorene (yield 0.75 g). $^1$H NMR (CDCl$_3$): δ 7.80 and 7.78 (each d, 1H, 4,5-H), 7.47 (d, 1H, J=8.1 Hz, H8), 7.34 (dd, 1H, J=8.1Hz, J=1.5Hz, H7), 7.31 (d, 1H, 1H, J=1.5 Hz, H1), 4.72 (s, 2H, CH$_2$Cl), 3.87 (s, 2H, H9), 1.41 (s, 18H, t-Bu) and 2,7-dichloromethyl-3,6-di-t-butylfluorene (yield 0.63 g). $^1$H NMR (CDCl$_3$): δ 7.87 (br s, 2H, 4,5-H), 7.34 (br s, 2H, 1,8-H), 4.75 (s, 4H, CH$_2$Cl), 3.95 (s, 2H, H9), 1.42 (s, 18H, t-Bu) as indicated by the following reaction:

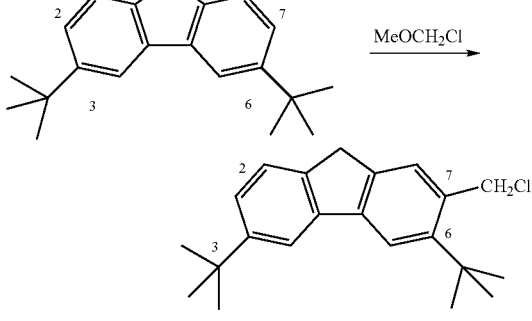

(20)

EXAMPLE 5

Reduction of 2,7-dichloromethane-3,6-di-tert-butyl-fluorene

To a solution of 2,7-di-chloromethyl-3,6-di-t-butylfluorene (0.75 g) in THF (15 ml) was added a small portion of LiAlH$_4$ (0.25 g) under stirring. The mixture was refluxed for 5 hours. The reaction was quenched with water and NaOH, and extracted with ether. The ether solution was evaporated under vacuum to produce a white solid with a yield of 0.69 g.

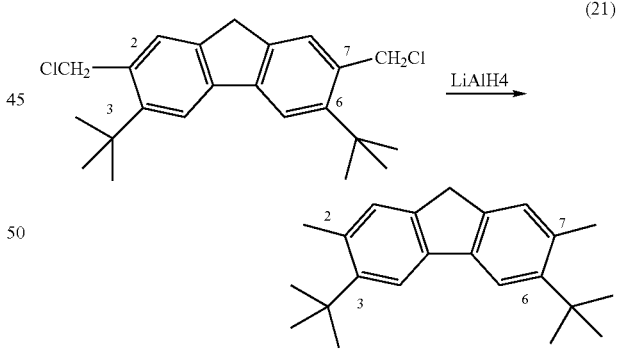

(21)

Examples 6 and 7 illustrate the synthesis of 2,2-[(cyclopentadienyl)-(2,7-di-phenyl-3,6-di-tert-butylfluorenyl)]-isopropylidene zirconium dichloride (catalyst component M1).

EXAMPLE 6

2,2-[(Cyclopentadienyl)-[(2,7-di-phenyl-3,6-di-tert-butylfluorenyl)]-propane Butyllithium (1.5 ml, 1.6M in hexane, 2.40 mmol) was added to 2,7-diphenyl-3,6-di-t-butyl-fluorene (0.95 g, 2.20 mmol) in THF (20 ml) at −78° C. The reaction mixture was allowed to warm to room temperature and stirred for 2.5 hours. The solvent was removed under vacuum. Ether (5 ml) was added and removed under vacuum. Ether (25 ml) was added and 6,6'-dimethylfulvene (0.23 g, 2.43 mmol) in ether (5 ml) was added to the reaction mixture at 0° C. The reaction was stirred at room temperature for 5 days. The reaction mixture was quenched with water, extracted with ether, dried over MgSO$_4$, and evaporated under vacuum to afford the residue which was purified by column chromatography (silica gel, hexane/CH$_2$Cl$_2$=5/1) and crystallized from hot hexane. The yield was 0.40 g, 34%. $^1$H NMR (CDCl$_3$): δ 7.91 and 7.30 (each s, 2H, 1,8- and 4,5-H (Flu), 7.35 (m, 10H, Ph), 6.76, 6.40 (m, 3H, Cp), 4.04 and 4.02 (s, 2H, H9), 3.00 and 2.78 (br s, 2H, CH2 Cp), 1.31 (s, 18H, t-Bu), 1.11 and 1.09 (s, 6H, Me). $^1$H NMR (CD$_2$Cl$_2$): δ 7.91 and 7.29 (each s, 2H, 1,8- and 4,5-H (Flu), 7.2-7.4 (m, 10H, Ph), 6.8-6.7, 6.40 (m, 3H, Cp), 4.02 (brs, 2H, H9), 3.00 and 2.78 (br s, 2H, CH2 Cp), 1.28 (s, 18H, t-Bu), 1.07 and 1.04 (s, 6H, Me). HPLC: 10.38 and 10.65 min.

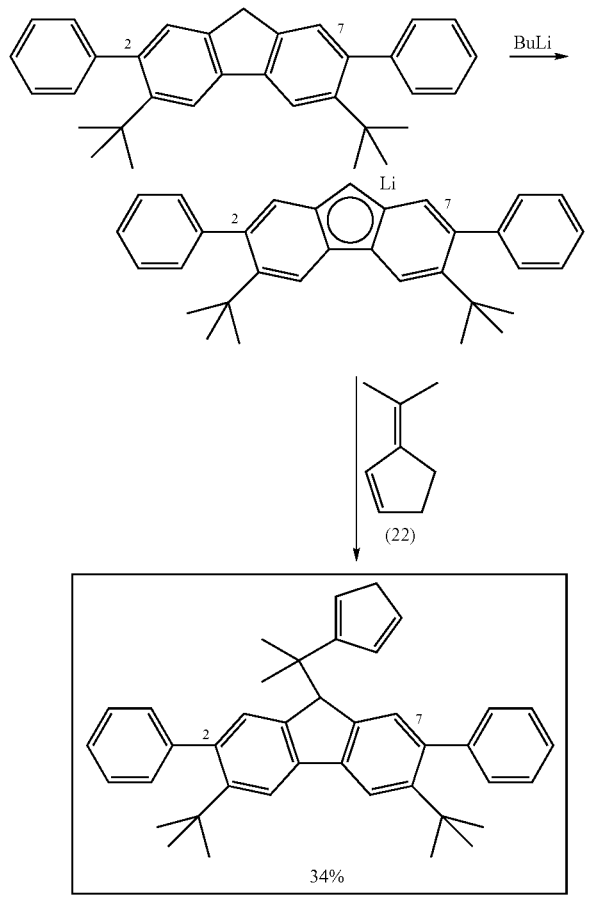

at −78° C. The reaction mixture was allowed to warm to room temperature and stirred for 2.5 hours. The solvent was evaporated under vacuum. Ether (5 ml) was added and removed under vacuum. ZrCl$_4$ (0.170 g, 0.76 mmol) was added at −78°. Ether (10 ml) was added to reaction mixture. The reaction mixture was allowed to warm to room temperature and stirred for 5 hours. The solvent was removed under vacuum to afford an orange solid, which was tested in propylene polymerization without purification. $^1$H NMR (C$_6$D$_6$): δ 8.14 (s, 2H, Flu-1,8), 7.4-7.2 (m, 12H, Ph, Flu-5,6), 6.04 and 5.69 (each m, 2H, Cp), 1.33 (s, 18H, t-Bu).

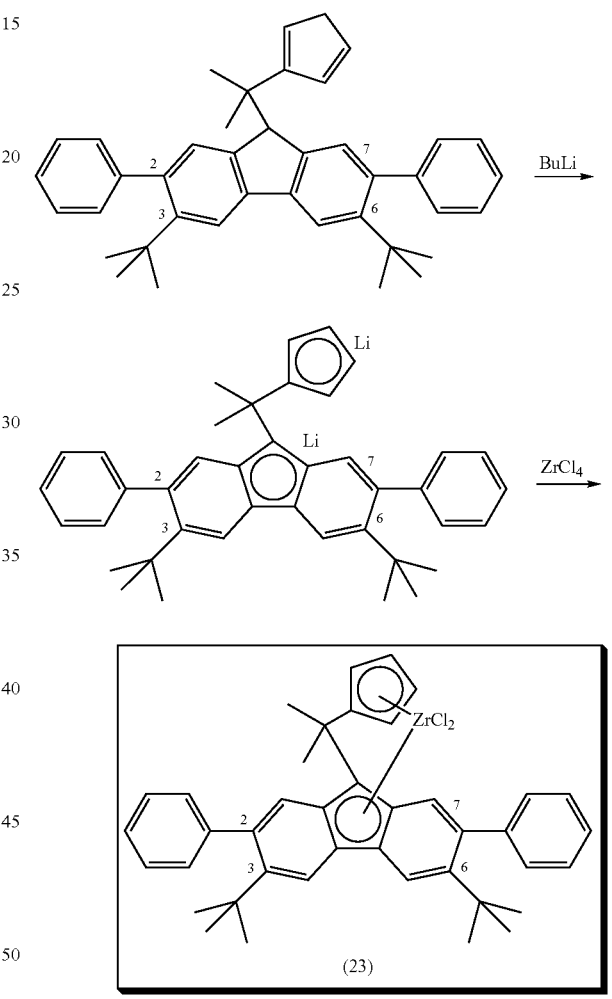

Examples 8-10 illustrate the synthesis of (4-tert-butyl-phenyl) [(cyclopentadienyl)(2,7-di-phenyl)-(3,6-di-tert-butyl-fluorenyl)]methane zirconium dichloride (catalyst M12).

EXAMPLE 7

2,2-[(Cyclopentadienyl)-(2,7-di-phenyl-3,6-di-tert-butylfluorenyl)]-propane zirconium dichloride (catalyst M1)

Butyllithium (1.0 ml, 1.6M in Et$_{20}$, 1.60 mmol) was added to 2,2-[(cyclopentadienyl)-[(2,7-d]-phenyl-3,6-di-tert-butylfluorenyl)]-propane (0.39 g, 0.73 mmol) in THF (10 ml)

EXAMPLE 8

6-(4-tetr-butyl-phenyl)-5-methyl-3-tert-butyl-fulvene

To a solution of methyl-tert-butylcyclopentadiene (4.42 g, 32.5 mmol) and 4-t-butyl-benzaldehyde (5.15 g) in absolute ethanol (30 ml) was added a small portions of sodium methoxide (4.0 g) under stirring. The mixture was stirred for 2 hours. The reaction was quenched with water and extracted with ether. The ether solution was evaporated under vacuum to give an orange liquid, which was purified by column chromatography (silica gel, hexane/CH$_2$Cl$_2$=8/1), providing a yield of 7.0 g. $^1$H NMR (CDCl$_3$): δ 7.55 (m, 2H, Ph), 7.48 (m, 2H, Ph), 7.02 (s, 1H, H—CPh), (m, 1H, H-6), 6.27 and 6.22 (br s, 2H, H-Cp), 2.18 (s, 3H, Me), 1.39 and 1.23 earh (s, 9H, t-Bu).

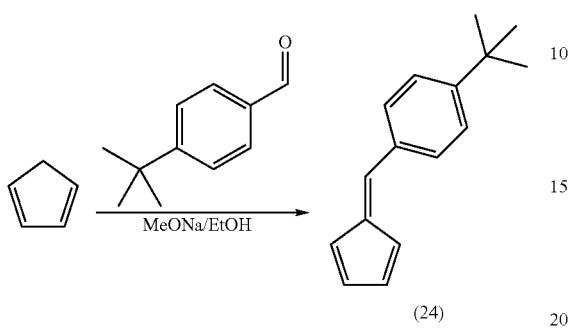

(24)

EXAMPLE 9

(4-tert-butyl-phenyl)[(cyclopentadienyl)-[(2,7-di-phenyl-3,6-di-tert-butylfluorenyl)]-methane Butyllithium (1.5 ml, 1.6M in hexane, 2.40 mmol) was added to 2,7-diphenyl-3,6-di-t-butyl-fluorene (1.02 g, 2.33 mmol) in ether (20 ml) at −78° C. The reaction mixture was allowed to warm to room temperature and stirred for 2.5 hours. 6-(4-tert-Butyl-phenyl)-fulvene (0.49 g, 2.33 mmol) in ether (5 ml) was added to the reaction mixture at −20° C. The reaction was stirred at room temperature for 2 hours. The reaction mixture was quenched with water, extracted with ether, dried over MgSO$_4$, and evaporated under vacuum to afford the residue, which was washed with hot ethanol.

EXAMPLE 10

(4-tert-Butyl-phenyl)[(cyclopentadienyl)(2,7-di-phenyl)-(3,6-di-tert-butyl-fluorenyl)]methane zirconium dichloride (catalyst M12)

Butyllithium (1.3 ml, 1.6M, 2.08 mmol) was added to (4-tert-butyl-phenyl)[(cyclopentadienyl)(2,7-di-phenyl)-(3,6-di-tert-butyl-fluorenyl)]methane (0.61 g, 0.95 mmol) in ether (10 ml) at −78° C. The reaction mixture was allowed to heat to room temperature and the reaction was continued for 2.5 hours. The solvent was removed under vacuum. ZrCl$_4$ (220 mg) was added to the reaction mixture. Toluene (15 ml) was added at −20° C. and the reaction was stirred at room temperature for night. The solvent was removed under vacuum.

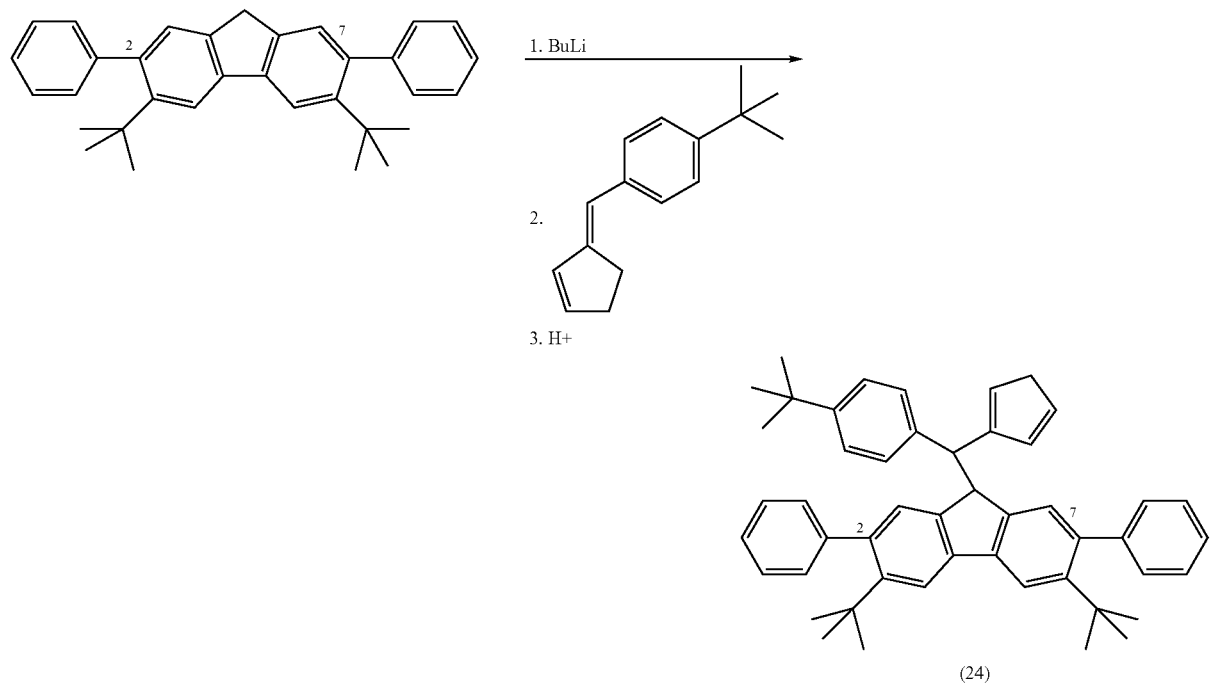

(24)

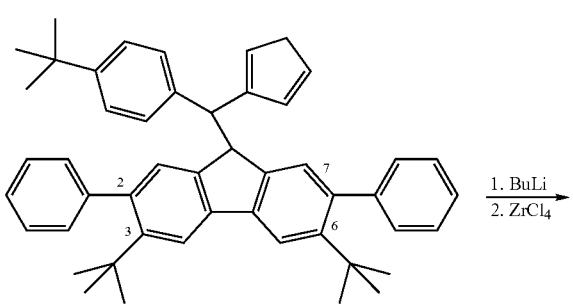

-continued

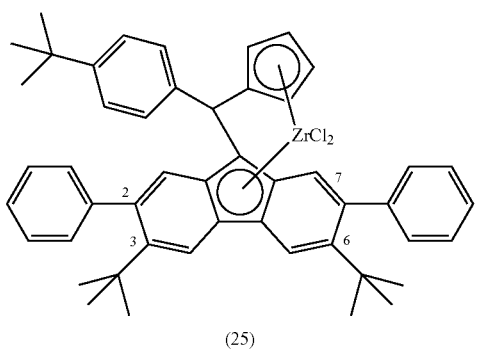

(25)

Catalysts M2-M11 and M13-M18 can be prepared as described in the foregoing Examples through the use of the corresponding 2,7-di-substituted-3,6-tert-butyl-fluorene and fulvene.

EXAMPLES 11-17

Homogeneous Polymerization with Catalyst M1

The polymerization was conducted in bulk propylene at 40, 60 and 70° C. in a 4 L reactor using the crude catalyst from Reaction 21 without purification. The polymerization behavior for the catalyst is set forth in Tables 1 through 3. The catalyst produced a polymer with activity of 30,000 gPP/gcat/h at 60° C. without hydrogen. In the presence of hydrogen (60 ppm) the activity increased up to 142,400 gPP/gcat/h. The catalyst produced syndiotactic polypropylene with pentad rrrr values of 85-92% (Table 4), melting temperature of 149-163° C. and molecular weight of 130,000 (Table 3). A broader molecular weight distribution (D) was also observed due to the presence of a low molecular weight fraction, a content of which could be decreased by fraction extraction of the polymer. Fraction extraction of the sample with hot hexane for 3 hours provided a polymer with a narrow molecular weight distribution (D=1.9), melting temperature of 153° C. and tacticity of 92% of rrrr pentad.

TABLE 1

Bulk Propylene Polymerization with Unsupported Catalyst M1

| Example | Catalyst mg | T, ° C. | Time, min | $H_2$, ppm | PP, g | Activity, gPP/g cat/h | MFR, dg/min |
|---|---|---|---|---|---|---|---|
| 11[a] | 20 | −10 | 180 | 0 | 2.0 | | |
| 12 | 7.0 | 40 | 60 | 0 | 42 | 6,000 | |
| 13 | 10 | 60 | 30 | 0 | 150 | 30,000 | 3.6 |
| 14[b] | | | | | | | |
| 15[c] | | | | | | | |
| 16 | 5.5 | 60 | 10 | 60 | 130 | 142,390 | 4.3 |
| 17 | 4.3 | 70 | 30 | 0 | 10 | 4,650 | |

[a]Polymerization at 1 atmosphere of propylene in toluene
[b]Crystallized fraction from xylene of sample 13
[c]Heptane extraction of sample 14

TABLE 2

DSC Data of Polypropylene

| Example | T melt, ° C. | T cryst, ° C. | Delta H melt, J/g | Delta H recryst, J/g |
|---|---|---|---|---|
| 11 | 163.0 | 109.0 | 29.6 | −39.3 |
| 12 | 160.4 | 98.6 | 37.0 | −97.9 |
| 13 | 149.4 | 89.6 | 46.3 | −59.6 |
| 14 | | | | |
| 15 | 152.7 | 97.6 | 44.7 | −49.0 |
| 16 | 154.4 | 109.6 | 40.8 | −109.6 |
| 17 | 146.0 | 101.0 | 29.2 | −48.9 |

TABLE 3

GPC Data of Polypropylene

| Example | Mn | Mw | Mz | D | D' |
|---|---|---|---|---|---|
| 11 | 7,909 | 222,922 | 1211,160 | 28[a] | 5.4 |
| 12 | 6,394 | 169,439 | 510,047 | 26.5[a] | 3.0 |
| 13 | 31,719 | 161,604 | 324,372 | 5.1 | 2.0 |
| 14 | 45,600 | 166,100 | 338,760 | 3.6 | 2.0 |
| 15 | 96,447 | 186,871 | 335,371 | 1.9 | 1.8 |
| 16 | 27,298 | 149,743 | 285,755 | 5.5 | 1.9 |
| 17 | 26,940 | 129,260 | 254,190 | 4.8 | 2.0 |

[a]bimodal

TABLE 4

Pentad Distributions for Syndiotactic Polypropylene

| | Example 12 | Example 13 | Example 14 | Example 16 | Example 17 |
|---|---|---|---|---|---|
| mmmm % | 2.1 | 0.3 | 0.3 | 0.4 | 0.4 |
| mmmr | 4.4 | 0.6 | 0.0 | 0.8 | 0.5 |
| rmmr | 2.5 | 0.8 | 0.6 | 1.0 | 1.0 |
| mmrr | 3.3 | 1.3 | 0.9 | 1.4 | 1.5 |
| xmrx | 9.2 | 3.0 | 1.5 | 3.2 | 4.0 |
| mrmr | 5.8 | 1.4 | 0.0 | 1.4 | 0.8 |
| rrrr | 65.2 | 87.5 | 92.0 | 86.3 | 84.9 |
| rrrm | 4.0 | 3.7 | 3.8 | 4.1 | 5.7 |
| mrrm | 3.6 | 1.4 | 0.9 | 1.3 | 1.2 |
| % meso | 18.2 | 4.6 | 2.1 | 5.3 | 5.1 |
| % racemic | 81.8 | 95.4 | 97.9 | 94.7 | 94.9 |
| % error | 7.1 | 2.3 | 1.4 | 2.6 | 3.0 |
| def/1000° C. | 90.9 | 22.8 | 10.4 | 26.5 | 25.3 |

EXAMPLES 18-25

Homogeneous Polymerization with Catalyst M12

The polymerizations in Examples 18-20 were conducted in bulk propylene using 10X-Multi-Clave reactor from Autoclave Engineers in 5 ml of bulk propylene in 30 ml glass vessels. The catalyst was activated with MAO (Zr/Al=1/1000-2000) prior to polymerization.

TABLE 5

Propylene polymerization with Catalyst M12 in 10X Multi-Clave reactors (bulk propylene, homogeneous, 60° C., 30 min, no H₂)

| Example | Catalyst (mg) | T°, C | Polymer, g | Activity, g/g//h | Tmelt, ° C. | Tcryst, ° C. | Mw/ 1000 | Mw/ Mn | Mz/ Mw |
|---|---|---|---|---|---|---|---|---|---|
| 18 | 0.15 | 50-60 | 1 | 13,300 | 158.7 | 96.3 | 206.7 | 2.6 | 1.9 |
| 19 | 0.45 | 40-50 | 3.6 | 10,526 | 161.9 | 99.0 | 278.8 | 2.9 | 1.8 |
| 20 | 0.9 | 20 | 5.7 | 6,333 | 160.0 | 96.3 | 300.0 | 2.6 | 1.8 | a The highest melting peak

EXAMPLE 21

Propylene Polymerization Under 1 atm with Catalyst M12

The propylene polymerization in Example 21 was conducted with 1.3 mg of catalyst M12, activated with 2 ml of 30% MAO, using the glass reactor under 1 atm of propylene in toluene solution at −10° C. for 3 hours. 1.6 g of polypropylene was isolated. Tmelt=171° C., T cryst=112.3° C., Mw=446,200, Mw/Mn=3.0, Mz/Mw=1.9.

TABLE 6

Tacticity of polypropylene samples

| TACTICITY, % | Example 20 | Example 19 | Example 21 |
|---|---|---|---|
| mmmm | 0.1 | 0.2 | 2.5 |
| mmmr | 0.3 | 0.0 | 1.1 |
| rmmr | 0.3 | 0.2 | 0.2 |
| mmrr | 0.6 | 0.5 | 0.4 |
| xmrx | 0.8 | 0.4 | 1.0 |
| mrmr | 0.2 | 0.0 | 0.1 |
| rrrr | 89.7 | 94.6 | 90.7 |
| rrrm | 6.1 | 3.2 | 3.0 |
| mrrm | 1.9 | 0.9 | 1.1 |
| % meso | 1.5 | 0.8 | 4.5 |
| % racemic | 98.5 | 99.2 | 95.5 |
| % error | 0.7 | 0.3 | 0.7 |
| def/1000 C. | 7.4 | 4.2 | 22.3 |

The polymerizations in Examples 22-25 were conducted in bulk propylene using a 2 L Zipper-Clave reactor from Autoclave Engineers. The reactor was charged with 300 g of bulk propylene prior to polymerization. The catalyst was activated with MAO (Zr/Al=1/1000-2000) prior to polymerization.

As can be seen from Examples 18-25, catalyst M12 produced syndiotactic polypropylene with pentad rrrr values of 88-95%, melting temperatures of 153-171° C., molecular weights of 154,000-300,000 at activities up to 530,000 gPP/Gcat/h.

EXAMPLES 26-29

Propylene Polymerization with Supported Catalyst M1

The catalyst M1 was supported on a silica support available from Asahi Glass Co., Ltd. under the designation H-121. The silica support had an average particle size of 12 microns. The catalyst supported on the silica with a 2 wt. % loading was tested at 60° C. for 1 hour in a 4 L reactor. The polymerization behavior for the unsupported catalyst is set forth in Tables 8 and 9. The hydrogen response of the supported catalyst was tested. The hydrogen response of the supported catalyst showed that the catalyst activity increased as the hydrogen levels increased (Table 8). The melting temperature of polymers produced in the presence of hydrogen was around 136-137° C. and is slightly dependent on hydrogen concentration. The molecular weight of the polymers showed a range of 99,000-78,000 for hydrogen levels of 0-75 ppm. In addition, the melt flow rate slightly increased from 31-44 g/10 min. with increasing the hydrogen concentration from 40 to 75 ppm. The supported catalyst produced a polymer with a narrow molecular weight distribution (D=2.1-2.6). Polymer produced using the supported catalyst showed good stereoregularity (% rrrr=82-83 in the presence of hydrogen) (Table 9).

TABLE 7

Bulk propylene polymerization with Catalyst M12 under homogeneous condition

| Example | Catalyst (mg) | T, ° C. | H2, ppm | Polymer, g | Activity, g/g//h | Tm, ° C. | MF, g/10 min | Mw/ 1000 | Mw/ Mn | Mz/ Mw | % Tol Sol |
|---|---|---|---|---|---|---|---|---|---|---|---|
| 22 | 0.3 | 50 | 30 | 56 | 373,333 | 159.7 | 1.0 | 219.8 | 2.6 | 1.8 | 0.5 |
| 23 | 0.5 | 60 | 60 | 65 | 260,000 | 157.7 | 1.9 | 173.4 | 2.2 | 1.8 | 0.9 |
| 24 | 0.2 | 60 | 30 | 53 | 530,000 | 155.7 | 1.5 | 176.9 | 2.2 | 1.8 | |
| 25 | 1.5 | 70 | 60 | 146 | 195,000 | 153.4 | 3.2 | 154.0 | 2.5 | 1.9 | 0.6 |

TABLE 8

Polymerization Test Results for Supported Catalyst M1

| Example | Cat mg | T, °C. | Time, min | H2, ppm | PP, g | Activity gPP/g cat/h | MFR, dg/min | T melt, °C. | Mn | Mw | Mz | D | D' |
|---|---|---|---|---|---|---|---|---|---|---|---|---|---|
| 26 | 40* | 60 | 60 | 0 | 4 | 100 | | 127.7 | 38,967 | 99,373 | 166,385 | 2.6 | 1.7 |
| 27 | 40* | 60 | 60 | 40 | 25 | 625 | 31 | 137.2/120.9 | 37,442 | 78,308 | 129,672 | 2.1 | 1.7 |
| 28 | 20* | 60 | 60 | 60 | 13 | 650 | 39 | 136.0/119.6 | 35,644 | 82,217 | 140,208 | 2.3 | 1.7 |
| 29 | 40* | 60 | 60 | 75 | 31 | 775 | 44 | 137.2/120.9 | 37,442 | 78,308 | 129,672 | 2.1 | 1.7 |

TABLE 9

Pentad Distributions for Syndiotactic Polypropylene Produced with Supported Catalyst

| | Example 26 | Example 27 | Example 28 | Example 29 |
|---|---|---|---|---|
| mmmm % | 0.4 | 0.1 | 0.2 | 0.0 |
| mmmr | 0.3 | 0.2 | 0.2 | 0.2 |
| rmmr | 1.2 | 1.3 | 1.3 | 1.3 |
| mmrr | 2.1 | 2.1 | 2.1 | 2.2 |
| xmrx | 4.6 | 4.5 | 4.6 | 4.3 |
| mrmr | 0.4 | 0.4 | 0.2 | 0.3 |
| rrrr | 77.9 | 82.3 | 82.6 | 83.2 |
| rrrm | 8.1 | 7.8 | 7.9 | 7.4 |
| mrrm | 5.0 | 1.2 | 1.1 | 1.1 |
| % meso | 5.4 | 5.2 | 5.1 | 4.9 |
| % racemic | 94.6 | 94.8 | 94.9 | 95.1 |
| % error | 3.5 | 3.5 | 3.6 | 3.4 |
| def/1000° C. | 17.5 | 17.7 | 17.8 | 17.2 |

TABLE 11

Tacticity of polypropylene produced with supported Catalyst M12

| | Example 31 | Example 33 |
|---|---|---|
| mmmm, % | 0.4 | 0.4 |
| mmmr | 0.3 | 0.3 |
| rmmr | 0.8 | 0.8 |
| mmrr | 1.9 | 1.8 |
| xmrx | 3.3 | 3.4 |
| mrmr | 0.5 | 0.0 |
| rrrr | 90.4 | 83.2 |
| rrrm | 1.9 | 8.1 |
| mrrm | 0.7 | 1.8 |
| % meso | 4.2 | 4.2 |
| % racemic | 95.8 | 95.8 |
| % error | 2.4 | 2.6 |
| def/1000° C. | 21.2 | 20.9 |

EXAMPLES 30-33

Propylene Polymerization with Supported Catalyst M12

The catalyst M12 was supported on silica supports available from Asahi Glass Co., Ltd. under the designation H-121 and G952. The catalyst supported on the silica with a 2 wt. % loading was tested at 60° C. for 30 minutes in 500 ml stainless reactor. The results in terms of polymerization parameters and polymer properties are shown in Tables 10 and 11.

TABLE 10

Propylene polymerization with Supported Catalyst M12

| Entry # | Support | Run # | H2, ppm | Polymer, g | Activity, g/g/cat/h | Tm, °C. | Tc, °C. | Mw/1000 | Mw/Mn | Mz/Mw |
|---|---|---|---|---|---|---|---|---|---|---|
| 30 | G952 | 1137-099-R3 | 10 | 6.1 | 610 | 142.0/128.3 | 89.3 | 105 | 2.5 | 1.8 |
| 31 | G952 | 1137-099-R4 | 60 | 7 | 700 | 142.4 | 89.3 | 96 | 2.8 | 1.9 |
| 32 | H-121-C | 1137-099-R5 | 10 | 1.8 | 180 | 139.0 | 87.3 | 105 | 2.7 | 1.8 |
| 33 | H-121-C | 1137-099-R6 | 60 | 3 | 300 | 141.4 | 86.6 | 96 | 2.5 | 1.8 |

Having described specific embodiments of the present invention, it will be understood that modifications thereof may be suggested to those skilled in the art, and it is intended to cover all such modifications as fall within the scope of the appended claims.

The invention claimed is:

1. A process for the polymerization of an ethylenically unsaturated monomer comprising:
   (a) providing a metallocene catalyst component characterized by the formula:

$$B(FluL)MQ_n \qquad (3)$$

wherein:
(i) Flu is a fluorenyl group substituted symmetrically with hydrocarbyl groups at at least the 2,7 positions and the 3,6 positions, wherein said substitutions at the 2,7 positions are selected from the group consisting of aryl groups and $C_1$ to $C_3$ alkyl groups;
(ii) L is a substituted or an unsubstituted cyclopentadienyl group, a substituted or unsubstituted indenyl group, a substituted or unsubstituted fluorenyl group, or a heteroorgano group XR in which X is a heteroatom from Group 15 or 16 of the Periodic Table, and R is an alkyl group, a cycloalkyl group or an aryl group containing from 1 to 20 carbon atoms;
(iii) B is a structural bridge between L and Flu imparting stereorigidity to the ligand structure (FluL);
(iv) M is a Group 4 or Group 5 transition metal;
(v) Q is selected from the group consisting of Cl, Br, I, an alkyl group, an amino group, an aromatic group and mixtures thereof; and
(vi) n is 1 or 2;
(b) providing an activating cocatalyst component;
(c) contacting said metallocene component and said cocatalyst component in a polymerization reaction zone with an ethylenically unsaturated monomer under polymerization conditions to produce a polymer product by the polymerization of said monomer; and
(d) recovering said polymer product from said reaction zone.

2. The process of claim 1 wherein said monomer comprises propylene and said polymer product is a polypropylene homopolymer or copolymer.

3. The process of claim 2 wherein said metallocene component of subparagraph (a) incorporates a cyclopentadienyl group and is characterized by the formula:

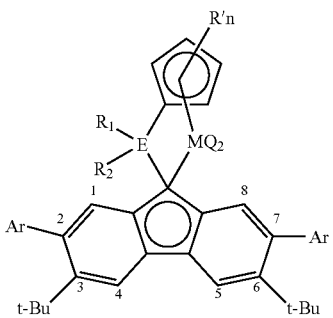

wherein:
Ar is a phenyl group or substituted phenyl group;
$R_1$ and $R_2$ are each independently a hydrogen, a $C_1$-$C_{10}$ alkyl group, or a cycloalkyl group, or an aryl group;
R' is a $C_1$-$C_4$ alkyl group or an aryl group;
n is a number from 0 to 4;
E is a —C— group or an —Si— group;
each of $R_1$ and $R_2$ is a $C_1$-$C_4$ alkyl group;
M is titanium, zirconium or hafnium; and
Q is chlorine, a methyl group, a phenyl group, or a substituted phenyl or benzyl group.

4. The method of claim 3 wherein said metallocene component exhibits bilateral symmetry and said polymer product is syndiotactic polypropylene.

5. The process of claim 3 wherein said metallocene component incorporates a cyclopentadienyl group which is monosubstituted or trisubstituted to provide a metallocene component which does not exhibit bilateral symmetry and wherein said polymer product is an isotactic polypropylene.

6. The process of claim 3 wherein said metallocene component incorporates a cyclopentadienyl group and is characterized by the formula:

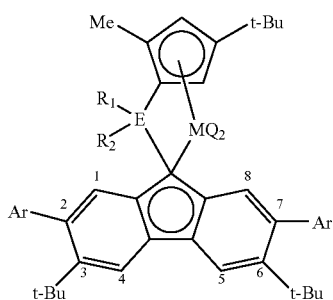

and said polymer product is a syndiotactic polypropylene with a melting temperature higher than 170° C.

7. The process of claim 3 wherein said polymer product is a syndiotactic polypropylene with a melting temperature higher than 150° C. and a crystallization temperature higher than 95° C.

* * * * *